(12) United States Patent
Chiang

(10) Patent No.: US 8,443,467 B2
(45) Date of Patent: May 21, 2013

(54) EARMUFF ASSEMBLY

(75) Inventor: Tsung-Pai Chiang, Taipei (TW)

(73) Assignee: Sound Team Enterprise Co., Ltd., Taipei (TW)

( * ) Notice: Subject to any disclaimer, the term of this patent is extended or adjusted under 35 U.S.C. 154(b) by 268 days.

(21) Appl. No.: 13/020,261

(22) Filed: Feb. 3, 2011

(65) Prior Publication Data

US 2011/0119804 A1 May 26, 2011

Related U.S. Application Data

(63) Continuation-in-part of application No. 12/216,278, filed on Jul. 2, 2008, now abandoned.

(30) Foreign Application Priority Data

Feb. 15, 2008 (TW) .............................. 97105463 A

(51) Int. Cl.
*A42B 1/06* (2006.01)
(52) U.S. Cl.
USPC ............................................................ 2/209
(58) Field of Classification Search
USPC ............ 2/10, 422, 423, 425, 171, 174, 195.5, 2/208, 209, 209.13; 128/864, 866; 181/129, 181/136; 381/309, 371, 374, 376, 377, 378, 381/379, 383; D29/112, 122
See application file for complete search history.

(56) References Cited

U.S. PATENT DOCUMENTS

| | | | |
|---|---|---|---|
| 1,087,704 A | 2/1914 | Adams-Randall | |
| 1,395,864 A * | 11/1921 | Pape | 381/379 |
| 1,398,958 A * | 12/1921 | Basch | 2/209 |
| 1,503,908 A * | 8/1924 | Manson | 381/378 |
| 1,513,924 A * | 11/1924 | Murdock | 381/379 |
| 1,583,540 A * | 5/1926 | Evans | 132/214 |
| 1,628,483 A | 5/1927 | Wiegand et al. | |
| 2,033,691 A * | 3/1936 | Douglass | 2/174 |
| 2,442,825 A * | 6/1948 | Rabushka | 2/195.5 |
| 2,572,746 A * | 10/1951 | Mougel | 2/209 |
| 2,640,199 A * | 6/1953 | Funk | 2/195.5 |
| 2,704,367 A * | 3/1955 | Gellman | 2/195.5 |
| 2,801,423 A * | 8/1957 | Shaw et al. | 2/209 |
| 3,112,005 A | 11/1963 | Shaw et al. | |
| 3,119,119 A | 1/1964 | Millinger et al. | |
| 3,193,841 A | 7/1965 | Haluska | |
| 3,335,720 A * | 8/1967 | Aileo | 128/866 |
| 3,432,861 A | 3/1969 | Flagg | |
| 3,461,463 A | 8/1969 | Beguin | |

(Continued)

FOREIGN PATENT DOCUMENTS

JP 56146719 11/1981

*Primary Examiner* — Shelley Self
*Assistant Examiner* — Jane Yoon
(74) *Attorney, Agent, or Firm* — Bacon & Thomas, PLLC

(57) ABSTRACT

An earmuff assembly includes a headband consisting of two headband elements each having two constraint lugs bilaterally located on one end and a coupling portion located on the opposite end, the coupling portion of one headband element being inserted through a groove on each constraint lug of the other headband element for allowing adjustment of the length of the headband, two ear cups, two connection devices that connect the coupling portions of the headband elements to the ear cups such that the angular positions of the ear cups are adjustable in the X-axis direction as well as in the Y-axis direction relative to the headband, and a soft fabric material covering the ear cups for optimal wearing comfort.

10 Claims, 16 Drawing Sheets

U.S. PATENT DOCUMENTS

| | | | | |
|---|---|---|---|---|
| 3,841,326 | A * | 10/1974 | Leight | 128/866 |
| 3,845,505 | A * | 11/1974 | Davison et al. | 2/209 |
| 3,875,592 | A * | 4/1975 | Aileo | 2/209 |
| 3,970,082 | A * | 7/1976 | Leight | 128/866 |
| 4,069,512 | A | 1/1978 | Palmaer | |
| 4,133,053 | A * | 1/1979 | Lundin | 2/209 |
| 4,796,307 | A | 1/1989 | Vantine | |
| 4,944,361 | A * | 7/1990 | Lindgren et al. | 181/129 |
| 5,046,192 | A * | 9/1991 | Ryder | 2/12 |
| 5,138,722 | A * | 8/1992 | Urella et al. | 2/209 |
| 5,185,807 | A * | 2/1993 | Bergin et al. | 381/378 |
| 5,293,647 | A * | 3/1994 | Mirmilshteyn et al. | 2/209 |
| 5,533,211 | A | 7/1996 | Mehrens | |
| 5,809,573 | A | 9/1998 | Bary | |
| 5,815,842 | A | 10/1998 | Hiselius | |
| 5,835,609 | A * | 11/1998 | LeGette et al. | 381/385 |
| 5,887,286 | A | 3/1999 | Waldron | |
| 6,016,574 | A | 1/2000 | Chen | |
| 6,055,672 | A * | 5/2000 | Natvig | 2/209 |
| 6,148,446 | A * | 11/2000 | Leight | 2/209 |
| 6,333,982 | B1 | 12/2001 | Sapiejewski et al. | |
| 6,629,579 | B1 * | 10/2003 | Hasegawa | 181/129 |
| 6,978,483 | B2 * | 12/2005 | Isom et al. | 2/209 |
| 7,024,013 | B1 | 4/2006 | Van Dam et al. | |
| 7,171,698 | B2 * | 2/2007 | Saffran | 2/209 |
| 7,172,052 | B2 | 2/2007 | Lenhard-Backhaus | |
| 7,283,641 | B2 | 10/2007 | Rolla | |
| 8,363,877 | B2 * | 1/2013 | Morisawa | 381/383 |
| 2002/0020003 | A1 * | 2/2002 | Le Gette et al. | 2/209 |
| 2002/0026661 | A1 * | 3/2002 | LeGette et al. | 2/209 |
| 2003/0037366 | A1 * | 2/2003 | Lindgren | 2/209 |
| 2003/0079275 | A1 * | 5/2003 | Woo et al. | 2/209 |
| 2003/0088905 | A1 * | 5/2003 | Bavetta et al. | 2/209 |
| 2003/0140397 | A1 * | 7/2003 | Isom et al. | 2/209 |
| 2003/0210801 | A1 * | 11/2003 | Naksen et al. | 381/370 |
| 2004/0125976 | A1 * | 7/2004 | Reneker | 381/372 |
| 2004/0172738 | A1 * | 9/2004 | Caine et al. | 2/209 |
| 2004/0184635 | A1 * | 9/2004 | Natvig | 381/371 |
| 2004/0213428 | A1 | 10/2004 | Lenhard-Backhaus | |
| 2004/0216946 | A1 * | 11/2004 | Lenhard-Backhaus | 181/129 |
| 2005/0015852 | A1 * | 1/2005 | Brhel | 2/209 |
| 2005/0183187 | A1 | 8/2005 | Jiang | |
| 2005/0241047 | A1 * | 11/2005 | Bavetta et al. | 2/209 |
| 2005/0246815 | A1 * | 11/2005 | LeGette et al. | 2/209 |
| 2006/0000006 | A1 * | 1/2006 | Gellis et al. | 2/209 |
| 2006/0015989 | A1 | 1/2006 | Faussett et al. | |
| 2006/0062417 | A1 * | 3/2006 | Tachikawa | 381/378 |
| 2006/0090246 | A1 * | 5/2006 | Cozens et al. | 2/209 |
| 2006/0206983 | A1 | 9/2006 | Isom et al. | |
| 2007/0044205 | A1 * | 3/2007 | Sato et al. | 2/209 |
| 2007/0107110 | A1 * | 5/2007 | LeGette et al. | 2/209 |
| 2007/0113320 | A1 * | 5/2007 | Saffran | 2/208 |
| 2007/0199133 | A1 | 8/2007 | Bavetta et al. | |
| 2007/0226877 | A1 * | 10/2007 | Hansson et al. | 2/208 |
| 2008/0141439 | A1 * | 6/2008 | Healy et al. | 2/209 |
| 2008/0307562 | A1 * | 12/2008 | Tipp | 2/209 |
| 2008/0307563 | A1 * | 12/2008 | Le Gette et al. | 2/209 |
| 2008/0307564 | A1 * | 12/2008 | Le Gette et al. | 2/209 |
| 2008/0307565 | A1 * | 12/2008 | Le Gette et al. | 2/209 |

* cited by examiner

EARMUFF ASSEMBLY

This application is a Continuation-In-Part of application Ser. No. 12/216,278, filed on Jul. 2, 2008, now pending. The patent application identified above is incorporated here by reference in its entirety to provide continuity of disclosure.

BACKGROUND OF THE INVENTION

1. Field of the Invention

The present invention relates to earmuffs and more particularly, to an earmuff assembly which allows convenient adjustment of the length of the headband and the angular positions of the ear cups to fit different wearing conditions, and is covered with a soft fabric material for optimal wearing comfort.

2. Description of the Related Art

In autumn and winter, people may dress in heavy clothes to protect the body against the cold. In addition to a fur coat, wind coat or snow coat, people may also wear a hat, gloves, scarf, muff and/or other accessories for warmth. However, the aforesaid warm-keeping devices cannot directly protect the ears against the cold. When exposing the ears to the cold weather, the ears may suffer from a freezing injury or become painful. More particularly, when the cold wind passes or when one is in a low temperature place, cold mountain or snowland area, exposing the ears to the freezing air may cause a serious injury.

U.S. Pat. No. 5,835,609 discloses an ear covering device, entitled "Ear Protection Device". As illustrated in FIG. 16, this design of ear protection device comprises a headband A and two ear cups B on each end. The headband A is contemplated to be flexible so that the space between opposite ear cups B may be enlarged to permit attachment of the covering device onto the back of the head. Each ear cup B includes a frusto-conical frame portion having a central opening therein. Fabric C covers the frusto-conical portion of the ear cups B as well as the flexible headband A.

This design of ear protection device is still not satisfactory in function and has drawbacks as follows:
1. The ear protection device can simply be attached to the user's head from the top side or the back.
2. The looped portions A1 protrude over the bottom side of the headband A. When the user wears the ear protection device, the protruding looped portions A1 are directly stopped against the user's head, causing the head to feel uncomfortable.
3. After adjustment of the length, the elements of the headband A may slip relative to the respective looped portions A1, and consequently, the ear cups B may fall from the ears accidentally.
4. The ear cups B are respectively fastened to the ends of the headband A by a respective small fastening member D. When the user adjusts the angle of each ear cup B relative to the ears, the connection area between the headband A and the ear cup B may break easily, losing the functionality of the ear protection device.
5. The ear cups B are not strong enough for positive positioning on the user's head around each ear to keep the ears well protected.
6. The ear cups B are respectively affixed to the ends of the headband A. When not in use, the ear protection device cannot be collapsed to reduce the size for storage. When storing or carrying the ear protection device, the ear protection device may be deformed or damaged accidentally by an external pressure.
7. The ear cups B are respectively affixed to the ends of the headband A and not detachable. The fabric C must be covered on the frusto-conical portion of the ear cups B and the flexible headband A prior to connection between the ear cups B and the flexible headband A, complicating the assembly process.

Therefore, it is desirable to provide an ear protection device, which eliminates the aforesaid drawbacks.

SUMMARY OF THE INVENTION

The present invention has been accomplished under the circumstances in view. It is the main object of the present invention to provide an earmuff assembly, which allows convenient adjustment of the length of the headband and the angular positions of the ear cups to fit different wearing conditions, and is covered with a soft fabric material for optimal wearing comfort.

To achieve this and other objects of the present invention, an earmuff assembly comprises a length adjustable headband consisting of two headband elements, two ear cups, two connection devices that connect the coupling portions of the headband elements to the ear cups in such a manner that the angular positions of the ear cups are adjustable in the X-axis direction as well as in the Y-axis direction relative to the headband, and a soft fabric material covering the ear cups for optimal wearing comfort. Thus, the user can adjust the length of the headband and the angle of the ear cups subject to the actual wearing requirements, assuring positive contact between the ears and the ear cups.

Further, each headband element comprises two constraint lugs bilaterally located on one end and a coupling portion located on the opposite end. The coupling portion of one headband element is inserted through a groove on each constraint lug of the other headband element so that the combined length of the headband elements of the headband is conveniently adjustable.

Further, each headband element comprises two sliding grooves bilaterally extending along the length between the two opposite ends thereof. Further, each headband element has a thickness gradually increasing in direction from the constraint lugs toward the coupling portion. When the two headband elements are arranged together, the constraint lugs of one headband element fit the sliding grooves of the other headband element, avoiding protrusion of the constraint lugs over the surface of the headband and keeping the outwardly curved outer surface and inwardly curved inner surface of each of the headband elements in a smoothly arched condition to fit the user's head positively and comfortably. When adjusting the length of the headband, no stress concentration will occur, avoiding headband deformation.

Further, the coupling portion of each headband element has a through hole pivotally connected to a pivot hole on each of two parallel ends of a U-shaped connection plate of one respective connection device by a respective pivot member such that each ear cup is biasable with the U-shaped connection plate of the respective connection device relative to the headband horizontally (X-axis) to one of 90°, 0° and 180° positions.

Further, the coupling portion of each headband element has chamfered edges so that each ear cup may be biased with the U-shaped connection plate of the respective connection device relative to the headband horizontally (in the X-axis direction) to any one of 90°, 0° and 180° positions.

Further, each ear cup comprises an elongated base frame, a rim, an insertion hole cut through two distal ends of the elongated base frame, and a plurality of locating holes transversely formed in the elongated base frame across the insertion hole. Each connection device comprises a substantially U-shaped connection plate pivotally connected to one headband element of the headband by a pivot member, and an elongated connection strip coupled to the U-shaped connection plate and fastened to the insertion hole of the elongated base frame of the respective ear cup. The elongated connection strip is inserted through an insertion slot on the U-shaped connection plate, having a round rod transversely located on and formed integral with one end thereof and pivotally positioned in a round rod groove in the U-shaped connection plate, and also having a plurality of locating teeth transversely located on and spaced along each of two opposite sides thereof remote from the round rod and selectively engaged with the locating holes of the elongated base frame of the respective ear cup.

Further, the two ear cups are detachably connected to the headband elements of the headband by the connection devices. Thus, the soft fabric material can be wrapped about the ear cups and the headband either after or before connection between the headband and the ear cups.

As the length of the headband is adjustable and the ear cups may be biased relative to the headband in the X-axis direction as well as the Y-axis direction, the earmuff assemblies can be received in a received condition with the two ear cups closely attached together to reduce the size, saving storage space and avoiding accidental damage.

DETAILED DESCRIPTION OF THE PREFERRED EMBODIMENT

Figure 1:
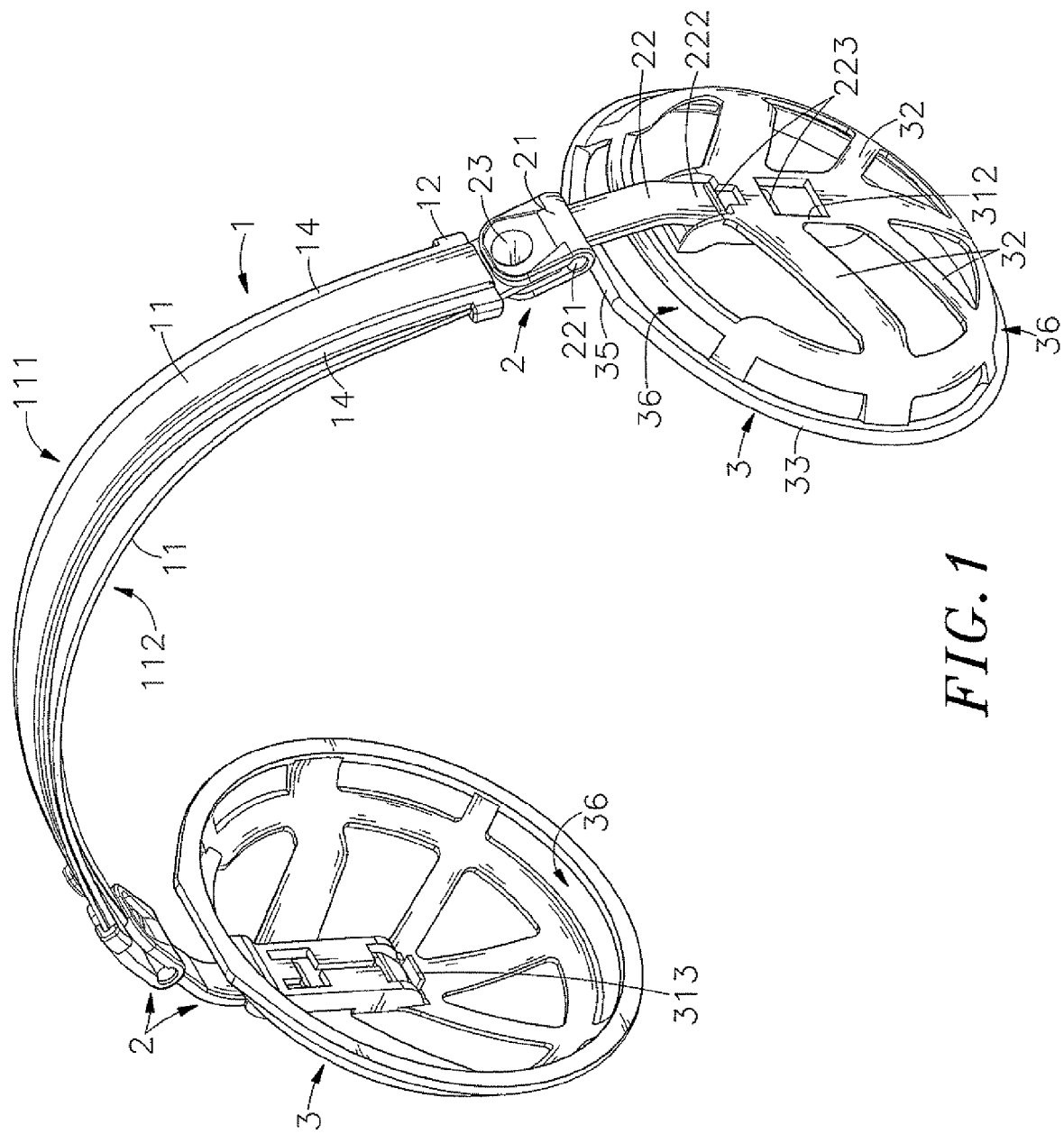
FIG. 1 is an elevational view of an earmuff assembly in accordance with the present invention (the soft fabric material excluded).
Figure 2:
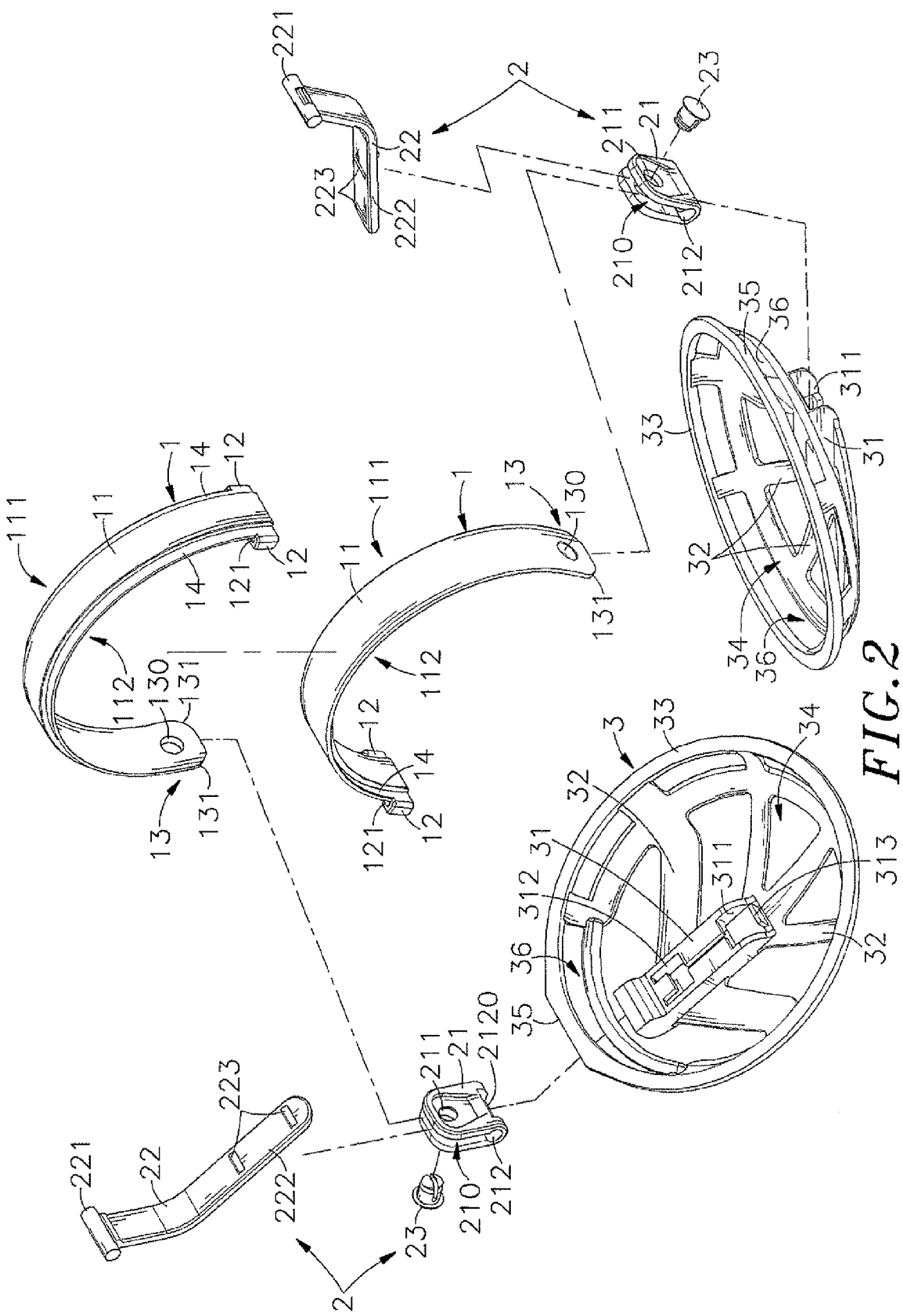
FIG. 2 is an exploded view of the earmuff assembly shown in FIG. 1.
Figure 10:
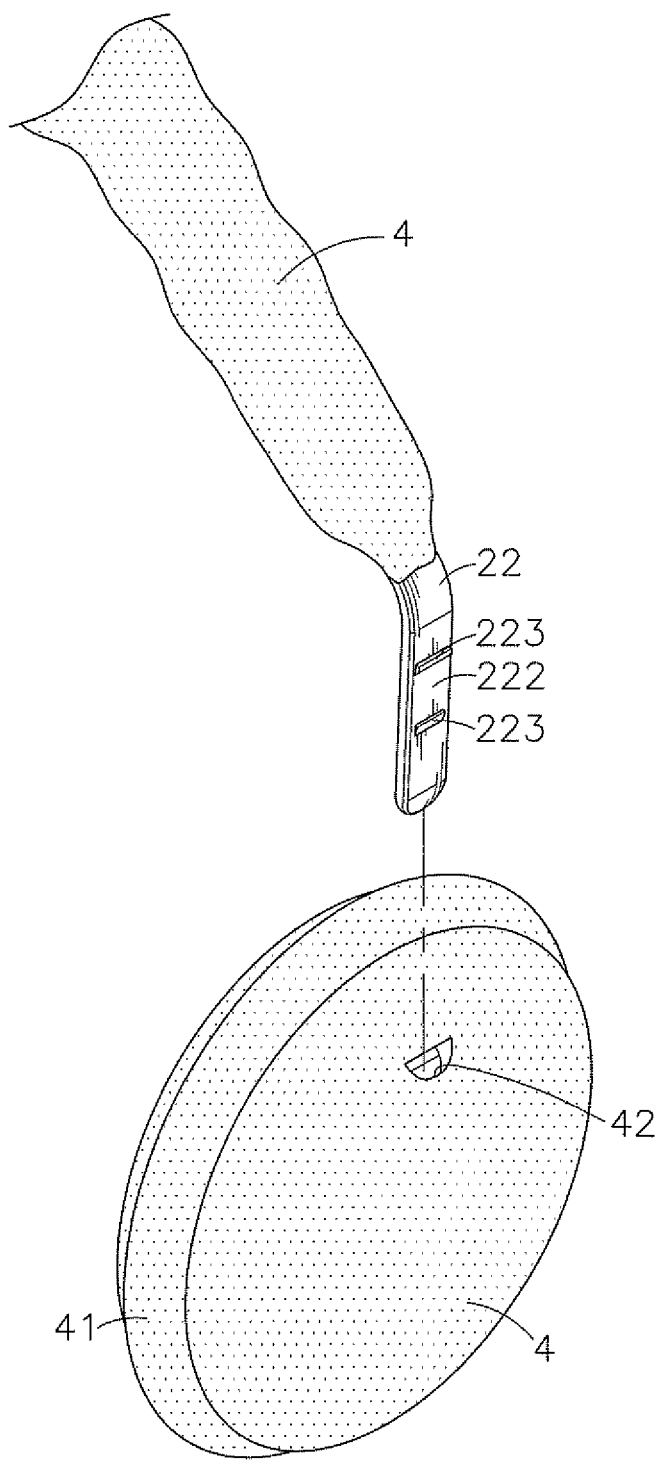
FIG. 10 is a schematic exploded view of the present invention, illustrating one mounting arrangement of the soft fabric material.

Referring to FIGS. 1, 2 and 10, an earmuff assembly in accordance with a first embodiment of the present invention is shown comprising a headband 1, two ear cups 3 for covering the user's ears respectively, two connection devices 2 that connect the ear cups 3 to the two distal ends of the headband 1, and a soft fabric material 4.

The headband 1 consists of two reversed headband elements 11. Each headband element 11 comprises two constraint lugs 12 bilaterally located on one end thereof, an insertion groove 121 defined in each of the two constraint lugs 12, a coupling portion 13 located on the other end thereof, and two sliding grooves 14 bilaterally extending along the length between the two opposite ends thereof. The coupling portion 13 has two chamfered edges 131 bilaterally located on the distal end thereof, and a through hole 130 spaced between the two chamfered edges 131.

Each connection device 2 consists of a substantially U-shaped connection plate 21, an elongated connection strip 22 and a pivot member 23. The U-shaped connection plate 21 comprises a flat positioning space 210 defined between the two parallel ends thereof, a pivot hole 211 cut through each of the two parallel ends across the flat positioning space 210, a round rod groove 212 transversely located on the middle part thereof inside the flat positioning space 210 and an insertion slot 2120 cut through the middle part. The elongated connection strip 22 comprises a strip body 222 insertable through the insertion slot 2120 of the U-shaped connection plate 21, a round rod 221 transversely located on and formed integral with one end of the strip body 222 for positioning in the round rod groove 212 of the U-shaped connection plate 21, and a plurality of locating teeth 223 transversely located on and spaced along each of the two opposite sides of the strip body 222 remote from the round rod 221.

Each ear cup 3 comprises an elongated base frame 31, a rim 33, an insertion hole 311 cut through two distal ends of the elongated base frame 31, a plurality of locating holes 312 transversely formed in the elongated base frame 31 across the insertion hole 311, a stop block 313 located on one end of the insertion hole 311 near the center of the respective ear cup 3, a plurality of ribs 32 extending in transverse and radial directions and connected with one another between the elongated base frame 31 and the rim 33, a rounded accommodation space 34 surrounded by the rim 33 and the ribs 32, a straight cutting edge 35 located on the periphery of the rim 33 adjacent to one end of the insertion hole 311 and remote from the stop block 313, and a plurality of plug holes 36 defined in between the rim 33 and the ribs 32.

The soft fabric material 4 is wrapped about each of the two connection devices 2 and each of the two ear cups 3 for direct contact with the user's ears.

Figure 3:
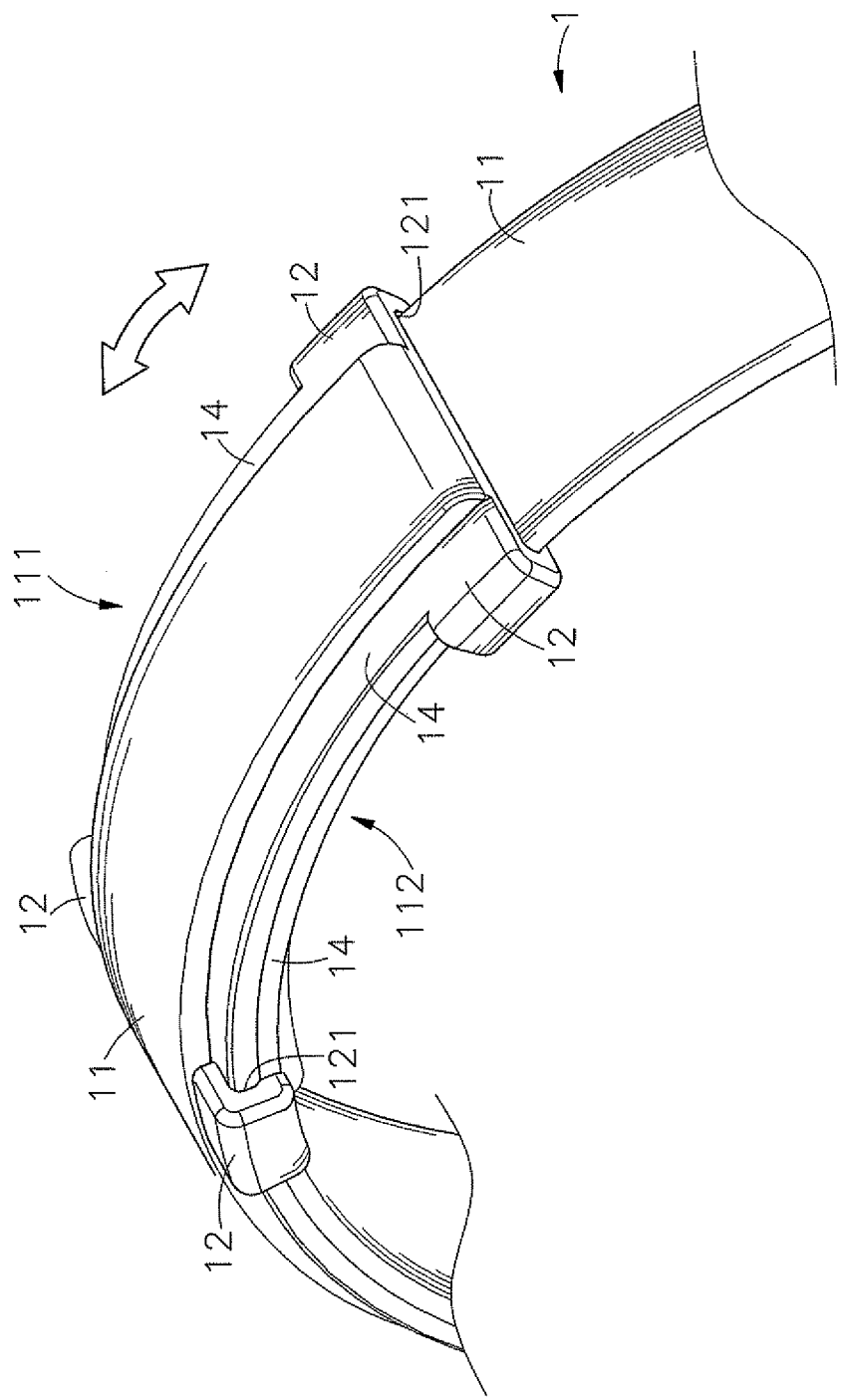
FIG. 3 is a schematic drawing of a part of the present invention, illustrating a length adjustment of the headband.
Figure 4:
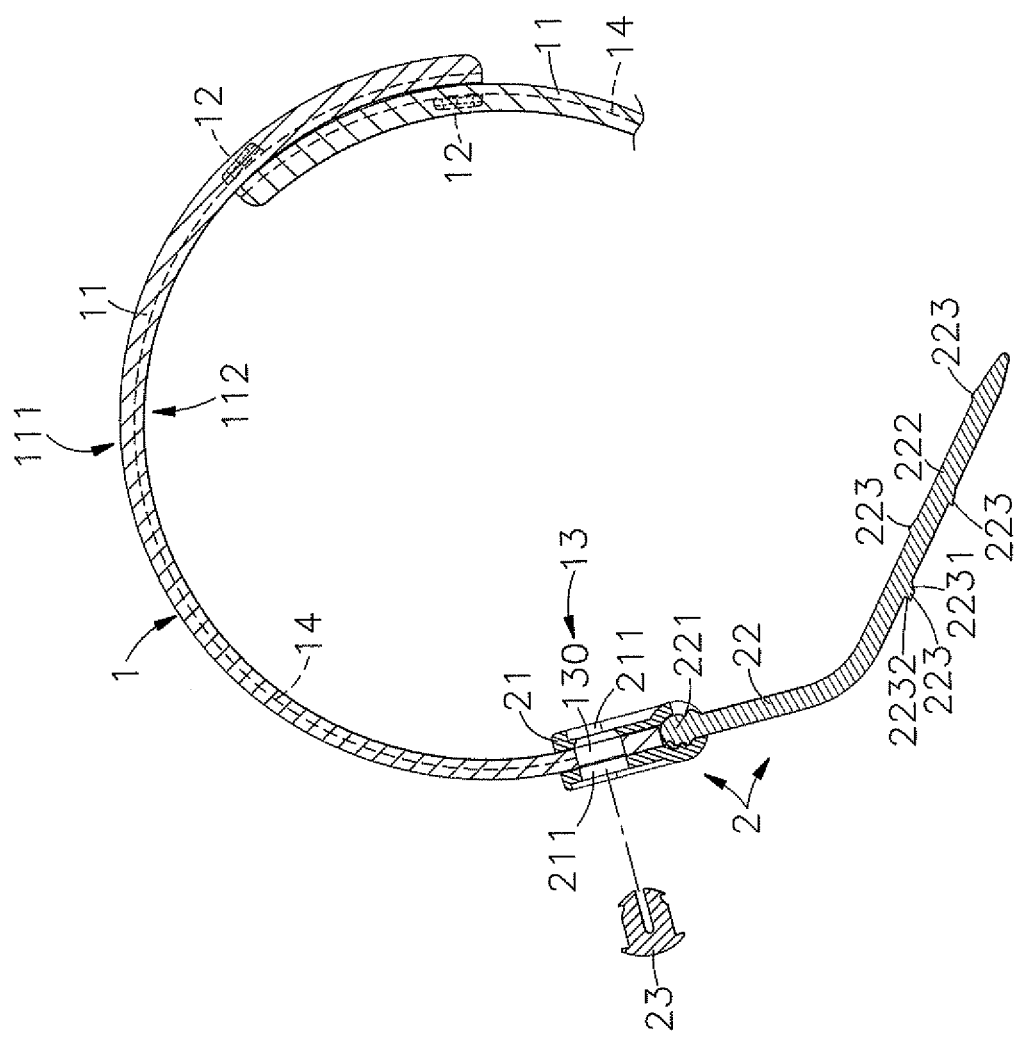
FIG. 4 is a schematic sectional view of the present invention, illustrating the mounting arrangement between the connection device and the headband.
Figure 5:
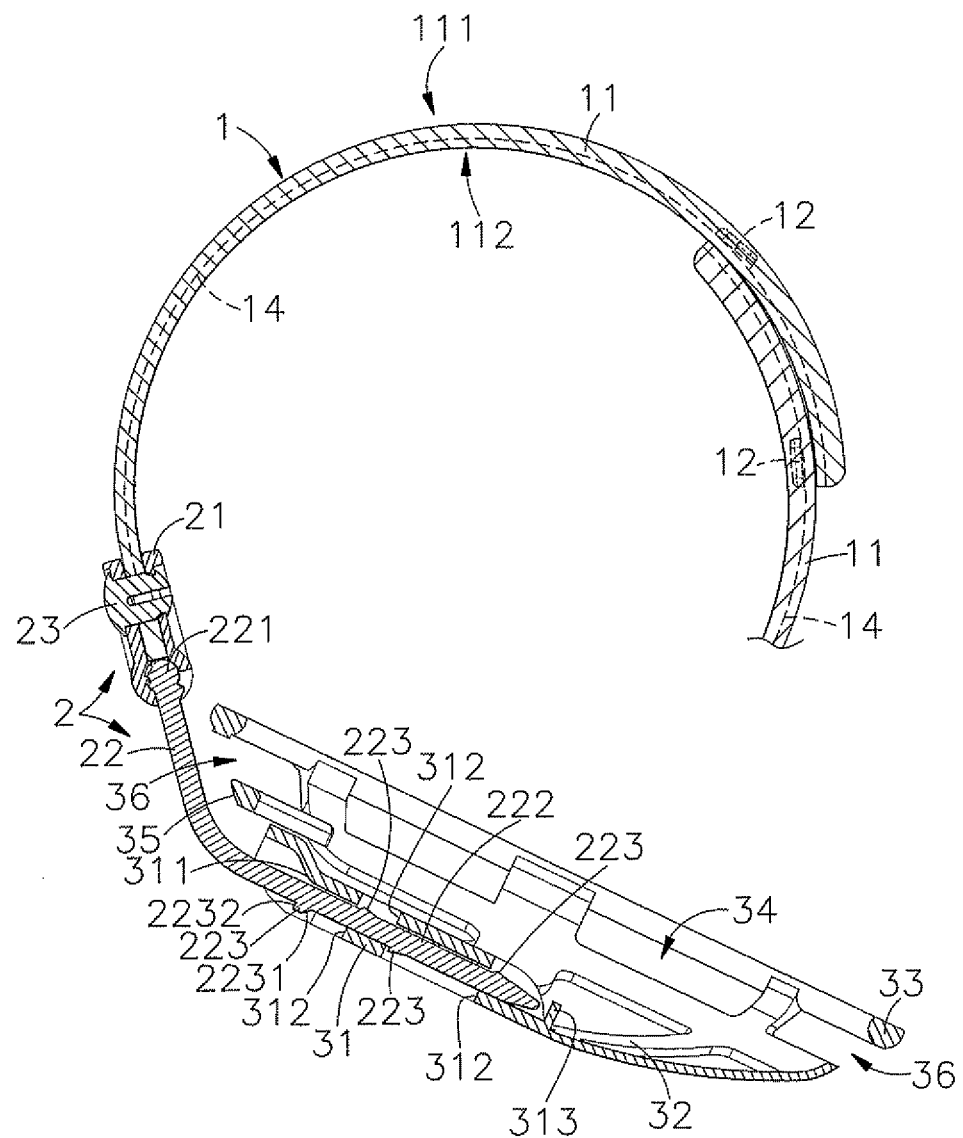
FIG. 5 is a schematic sectional view of the present invention, illustrating the mounting arrangement between the connection device and the ear cup.

The assembly process of the earmuff assembly will be described hereinafter with reference to FIGS. 3-5. At first, attach the two headband elements 11 of the headband 1 together, and insert the coupling portion 13 of one headband element 11 through the insertion grooves 121 of the constraint lugs 12 of the other headband element 11 to have the respective sliding grooves 14 be relatively slidably coupled to the respective insertion grooves 121 (see FIG. 3), and then insert the strip bodies 222 of the elongated connection strips 22 of the connection devices 2 through the insertion slots 2120 of the associating U-shaped connection plates 21 to have the round rods 221 of the respective the elongated connection strips 22 be positioned in the round rod grooves 212 of the associating U-shaped connection plates 21. Then insert the coupling portions 13 of the headband elements 11 of the headband 1 into the flat positioning spaces 210 of the U-shaped connection plates 21 of the connection devices 2 respectively, and then fasten the respective pivot members 23 to the pivot holes 211 of the U-shaped connection plates 21 of the connection devices 2 and the through holes 130 of the coupling portions 13 of the headband elements 11 of the headband 1 respectively to pivotally connect the headband elements 11 to the U-shaped connection plates 21 of connection devices 2 respectively (see FIG. 4). Then insert the strip bodies 222 of the elongated connection strips 22 of the connection devices 2 into the insertion holes 311 of the elongated base frames 31 of the ear cups 3 respectively to have the strip bodies 222 be respectively stopped against the respective stop blocks 313 in the respective elongated base frames 31 and the transversely extending locating teeth 223 of the strip bodies 222 be respectively engaged into the respective locating holes 312 (see FIG. 5).

Referring to FIGS. 4 and 5 again, each transverse locating tooth 223 has a beveled guide face 2231 located on the front side thereof and a vertical stop edge 2232 located on the rear side thereof. When inserting the strip bodies 222 of the elongated connection strips 22 of the connection devices 2 into the insertion holes 311 of the elongated base frames 31 of the ear cups 3, the beveled guide faces 2231 of the transversely extending locating teeth 223 facilitates forward movement of the respective strip bodies 222 in the respective insertion holes 311 relative to the respective elongated base frames 31. When the beveled guide face 2231 of one transverse locating tooth 223 is moved over one end of one respective insertion hole 311 of the elongated base frames 31, the vertical stop edge 2232 prohibits the respective transverse locating tooth 223 from backward movement with the respective elongated connection strip 22 relative to the respective elongated base frames 31.

Subject to the sliding coupling arrangement between the respective sliding grooves 14 and the respective insertion grooves 121, the two headband elements 11 can be moved axially relative to each other to adjust the length of the headband 1. Further, each headband element 11 has a thickness gradually increasing in direction from the constraint lugs 12 toward the coupling portion 13, enabling the two headband elements 11 to fit the user's head positively and comfortably. Further, thinning the wall thickness of the two opposite lateral sides of each of the headband elements 11 form the sliding grooves 14. When the two headband elements 11 are arranged together, the constraint lugs 12 of one headband element 11 fit the sliding grooves 14 of the other headband element 11, avoiding protrusion of the constraint lugs 12 over the surface of the headband 1 and keeping the outwardly curved outer surface 111 and inwardly curved inner surface 112 of each of the headband elements 11 in a smoothly arched condition.

Figure 6:
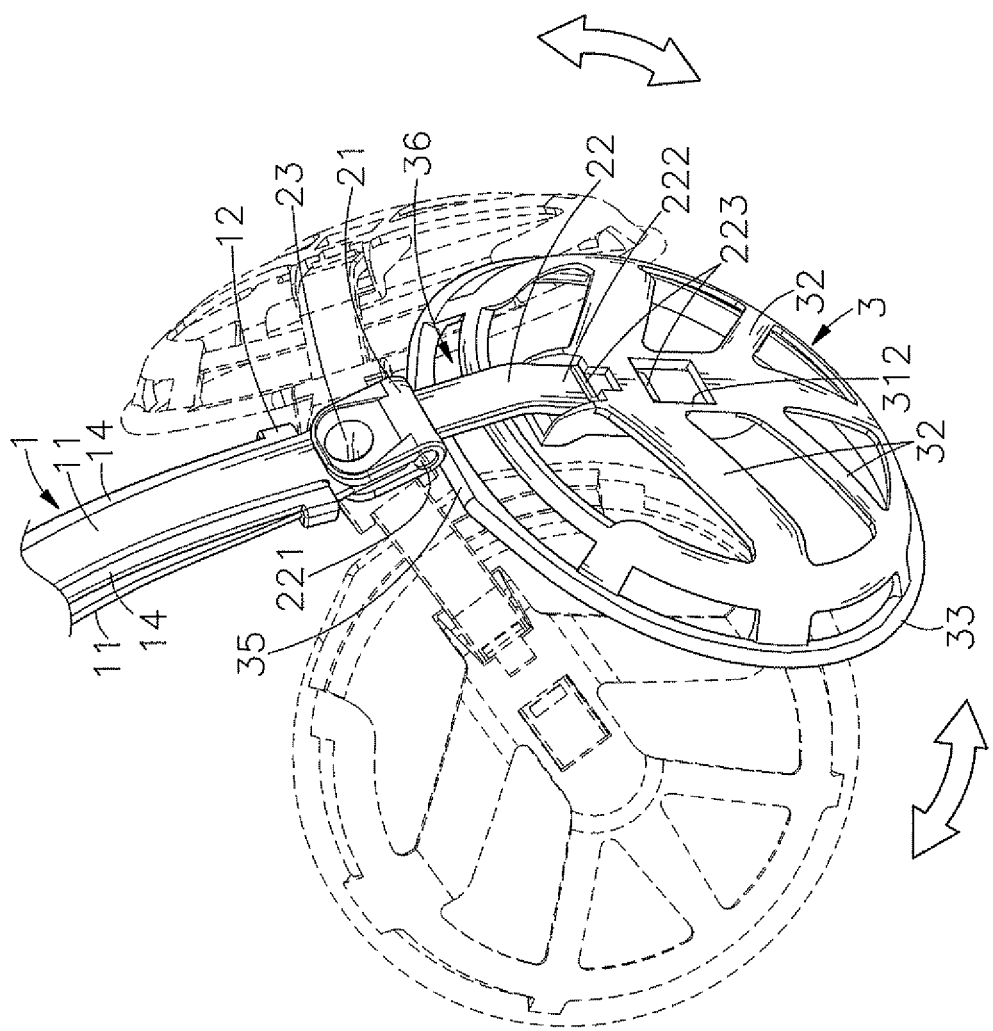
FIG. 6 is a schematic sectional view of the present invention, illustrating angular adjustment of the ear cup in the X-axis direction relative to the headband.
Figure 7:
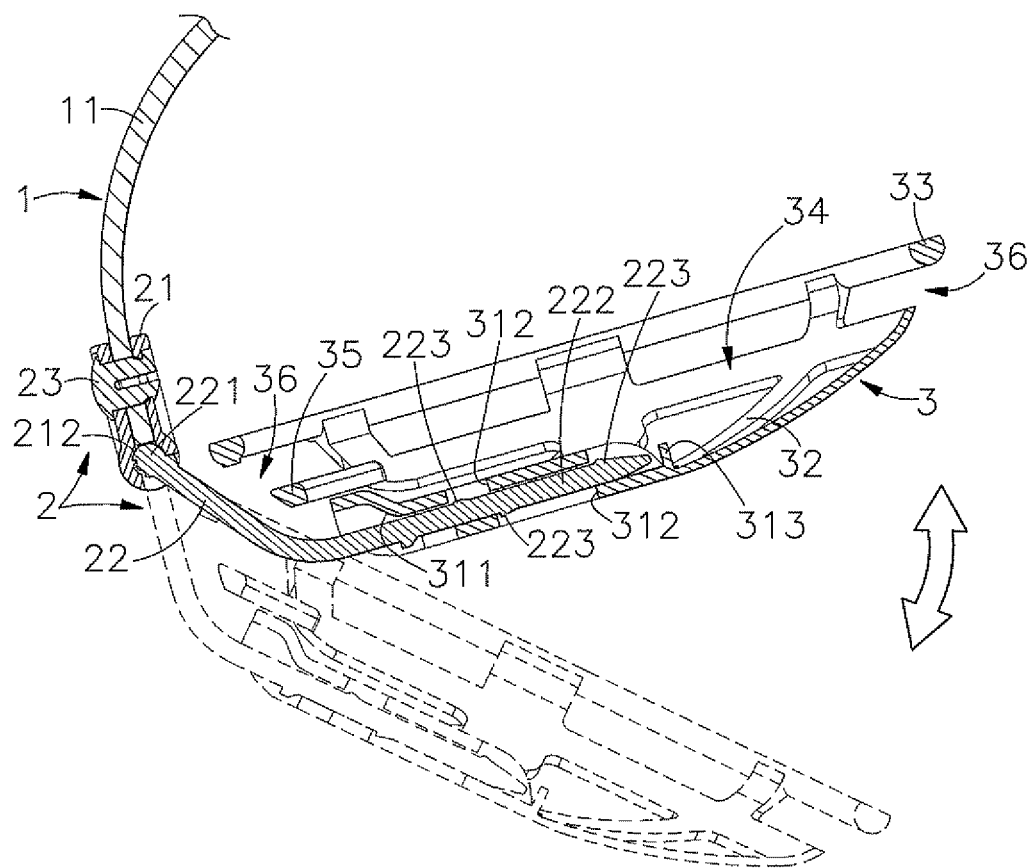
FIG. 7 is a schematic sectional view of the present invention, illustrating angular adjustment of the ear cup in the Y-axis direction relative to the headband.

Further, as stated above, the two pivot members 23 are respectively fastened to the pivot holes 211 of the U-shaped connection plates 21 of the connection devices 2 and the through holes 130 of the coupling portions 13 of the headband elements 11 of the headband 1 to pivotally connect the headband elements 11 to the U-shaped connection plates 21 of the connection devices 2. Thus, the headband elements 11 can be respectively turned about the respective pivot members 23 in the horizontal (X-axis) direction to selectively adjust the ear cups 3 to any one of the 0°, 90° and 180° positions (see FIG. 6). Subject to the design of the chamfered edges 131 of the of the headband elements 11 for stopping against the periphery of the round rods 221 of the elongated connection strips 22 of the respective connection devices 2, the ear cups 3 can be positively positioned in one of the 0°, 90° and 180° positions. Further, subject to the pivotal connection between the round rod 221 of the elongated connection strip 22 of each connection device 2 and the round rod groove 212 of the associating U-shaped connection plate 21, each ear cup 3 can be biased with the connected elongated connection strip 22 relative to the associated U-shaped connection plate 21 and the headband 1 in the vertical (Y-axis) direction (see FIG. 7). Thus, the user can adjust the angles of the ear cups 3 relative to the headband 1 conveniently when wearing or storing the earmuff assembly.

Figure 8:
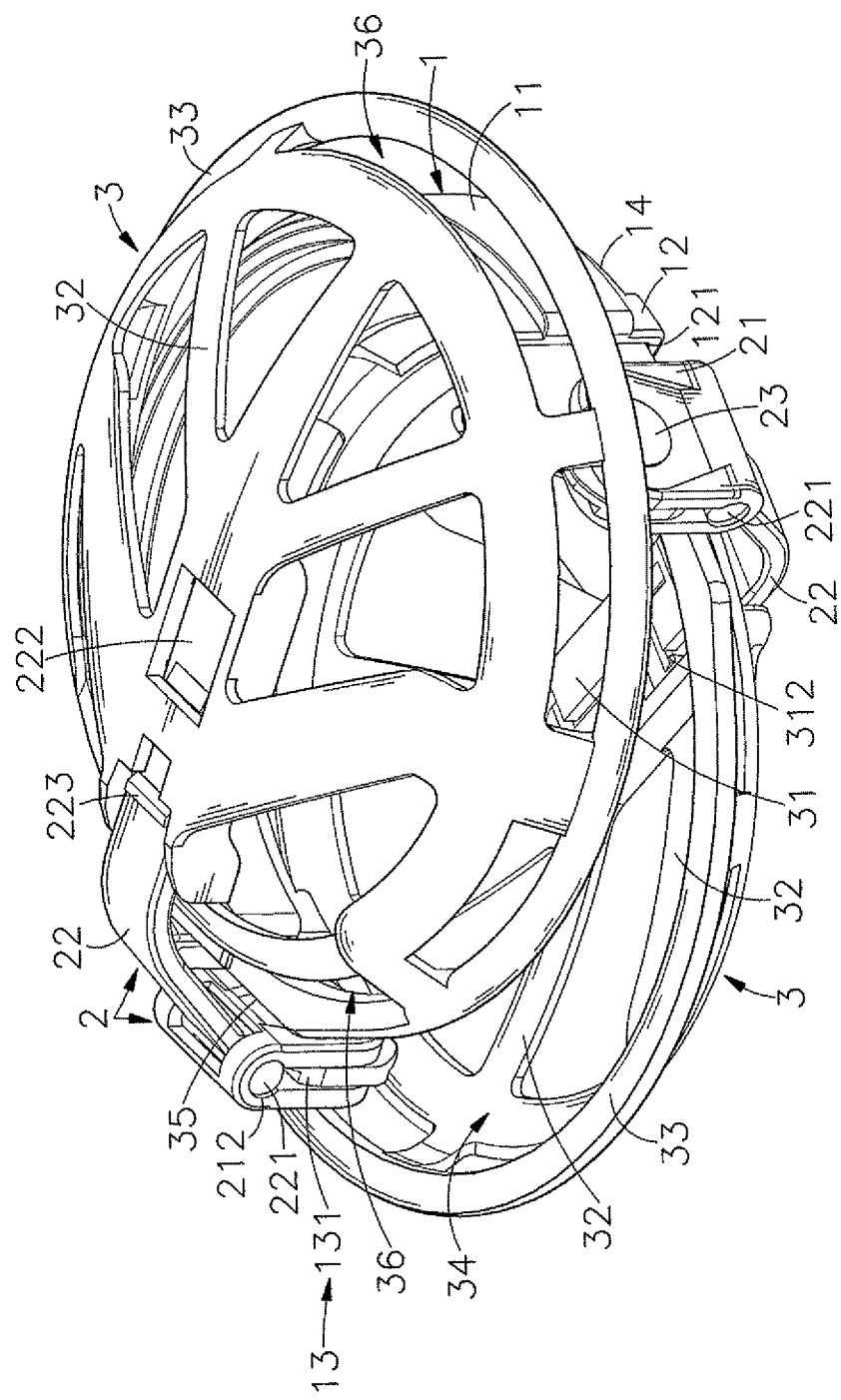
FIG. 8 is a schematic elevational view of the present invention, illustrating the earmuff assembly received in a first received condition (the soft fabric material excluded).
Figure 9:
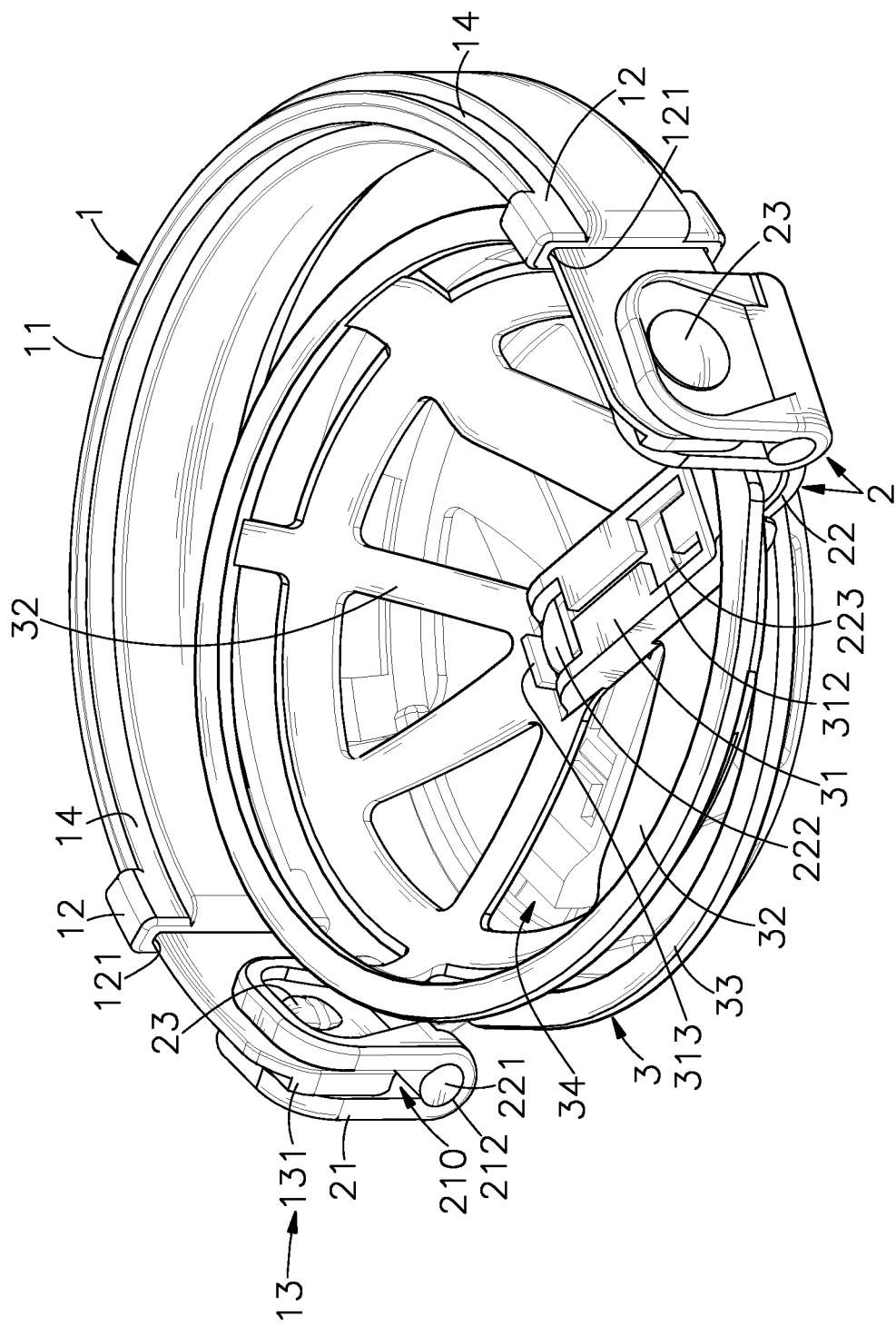
FIG. 9 is a schematic elevational view of the present invention, illustrating the earmuff assembly received in a second received condition (the soft fabric material excluded).

Referring to FIGS. 8 and 9, when the earmuff assembly is not used, it can be arranged in one of two received conditions. The user can shorten the combined length of the headband elements 11 of the headband 1, and then bias one ear cup 3 with the connected elongated connection strip 22 relative to the associated U-shaped connection plate 21 and the headband 1 to have the two ear cups 3 be attached together in a reversed manner (see FIG. 8). Alternatively, the user can shorten the combined length of the headband elements 11 of the headband 1, and then bias the ear cups 3 to have one ear cup 3 be received in the other ear cup (see FIG. 9). Subject to the functioning of the connection devices 2, the user can conveniently adjust the angular positions of the ear cups 3 relative to the headband 1 to fit different wearing requirements, assuring wearing comfort. The user can also conveniently receive the earmuff assembly in a received condition to reduce space occupation, avoiding structural damage or deformation during storage.

Referring to FIG. 10, after connection between the headband 1 and the connection devices 2, the soft fabric material 4 is wrapped about the headband 1 and the connection devices 2 to let the elongated connection strips 22 of the connection devices 2 be exposed to the outside of the soft fabric material 4. During the assembly process, two pieces of the soft fabric material 4 are respectively attached to the front and back sides of each of the ear cups 3, and then peripherally stitched together. A finding tape 41 is seamed to the peripheral edges of the stitched pieces of the soft fabric material 4, and then an opening 42 is made on one piece of the soft fabric material 4 corresponding to the insertion hole 311 of the elongated base frame 31 of the associating ear cup 3. After connection between the headband 1 and the connection devices 2 is completed, the strip body 222 of each connection device 2 is directly inserted through the opening 42 of the soft fabric material 4 at each ear cup 3 into the insertion hole 311 of the elongated base frame 31 of the associating ear cup 3 to connect the associating ear cup 3 to the headband 1 (see FIG. 10). Because the soft fabric material 4 is separately made and then fastened to the ear cups 3 of the earmuff assembly, different designs of the soft fabric material 4 can be selectively used.

Figure 11:
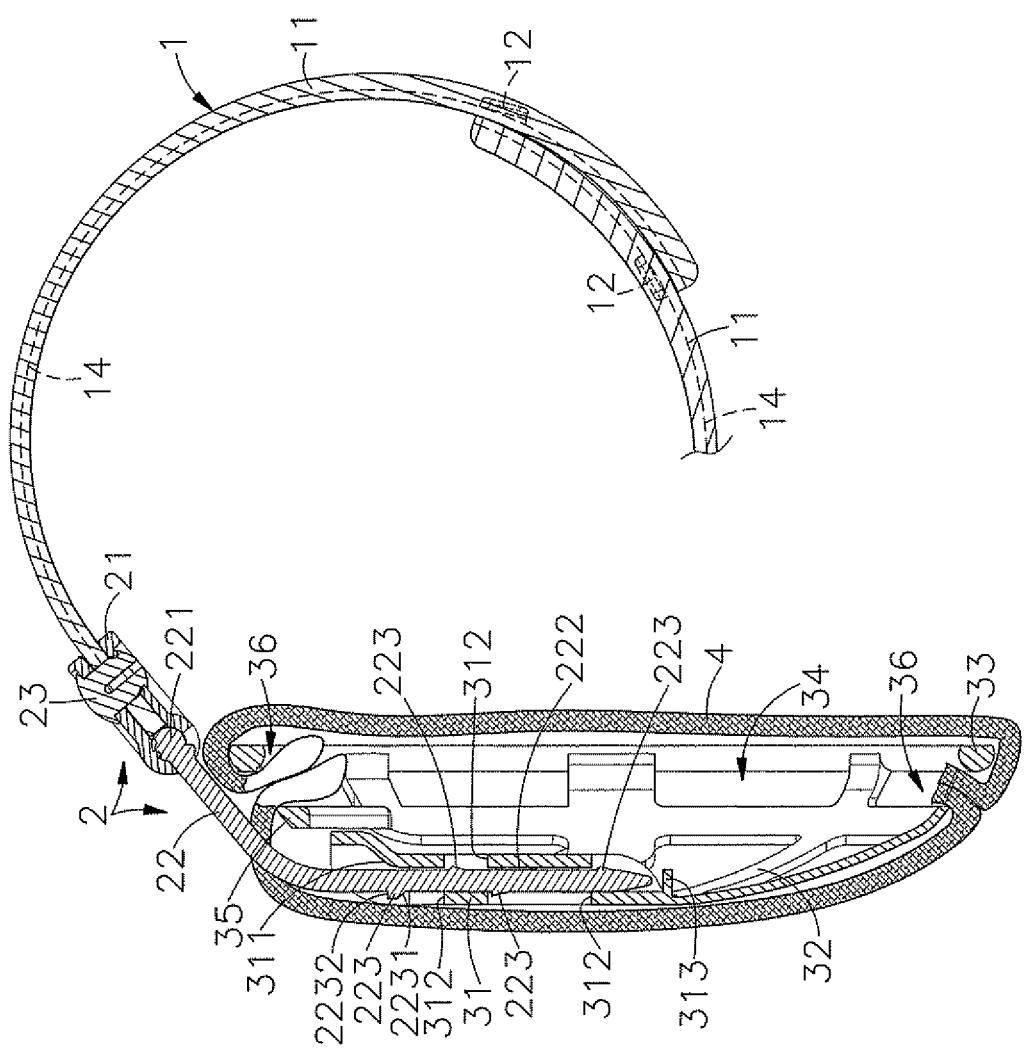
FIG. 11 is a schematic sectional view of the present invention, illustrating another mounting arrangement of the soft fabric material.

Referring to FIG. 11, two pieces of the soft fabric material 4 can be peripherally stitched together to form a pocket that fits the configuration of the ear cups 3, and then each pocket thus made is turned inside out and sleeved onto one respective ear cup 3. The opposing unstitched border edges around the opening of each pocket are turned inwards and selectively inserted into the plug holes 36 between the rim 33 and ribs 32 of the associating ear cup 3. The unstitched border edges of each pocket can be inserted into the plug holes 36 of the associating ear cup 3 adjacent to the straight cutting edge 35. Alternatively, the unstitched border edges of each pocket can be inserted into the plug holes 36 of the associating ear cup 3 opposite to the straight cutting edge 35.

Figure 12:
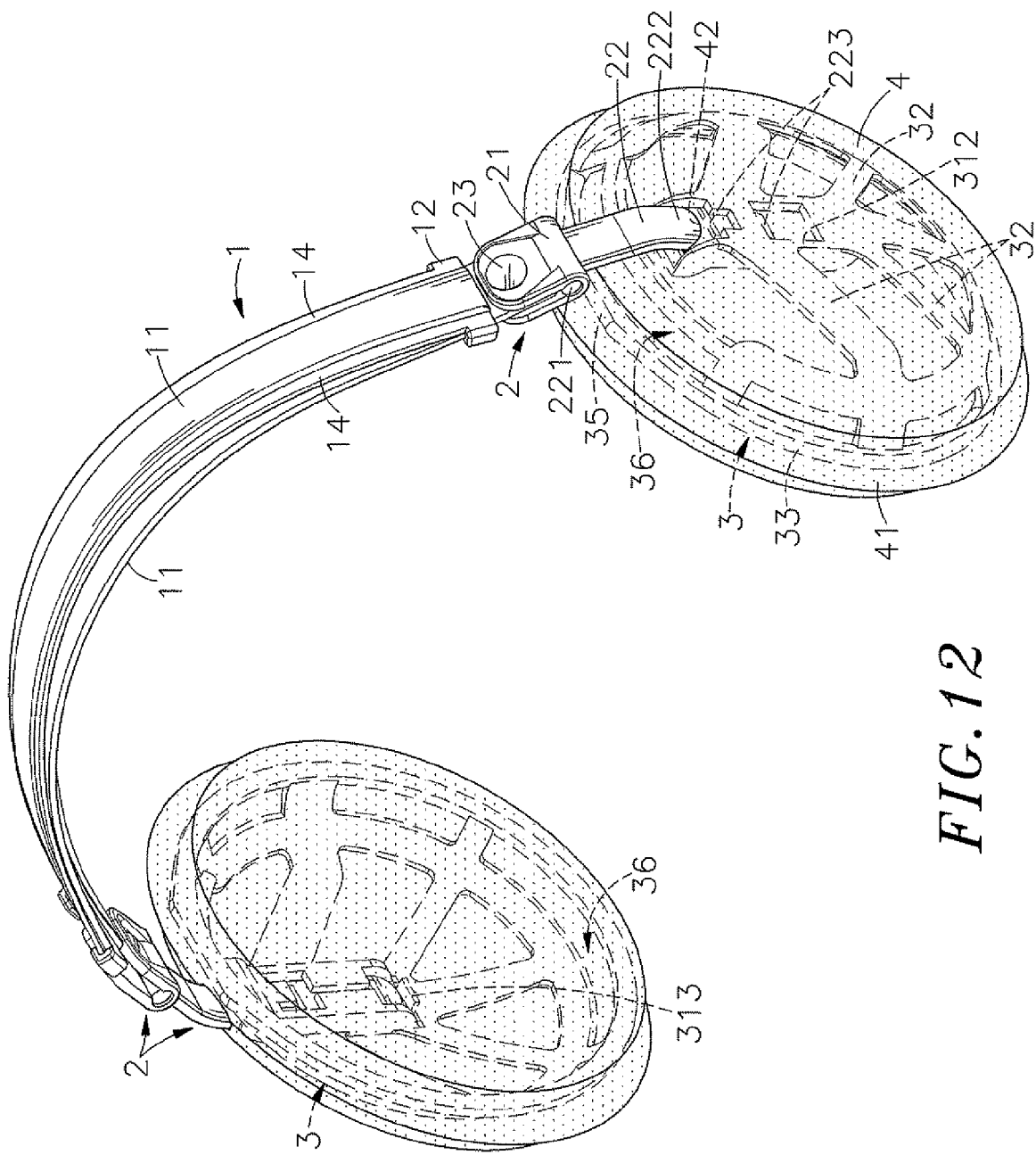
FIG. 12 is a schematic perspective view of the present invention, illustrating still another mounting arrangement of the soft fabric material.

Referring to FIG. 12, the soft fabric material 4 can simply cover the ear cups 3 to let a part of each of the elongated connection strips 22 of the connection devices 2, the U-shaped connection plates 21 of the connection devices 2, and the headband 1 be exposed to the outside. Pieces of the soft fabric material 4 can be stitched together, overedge seamed, and then put on each ear cup 3. Alternatively, pieces of the soft fabric material 4 can be stitched together and then turned inside out, and then put on each ear cup 3.

Figure 13:
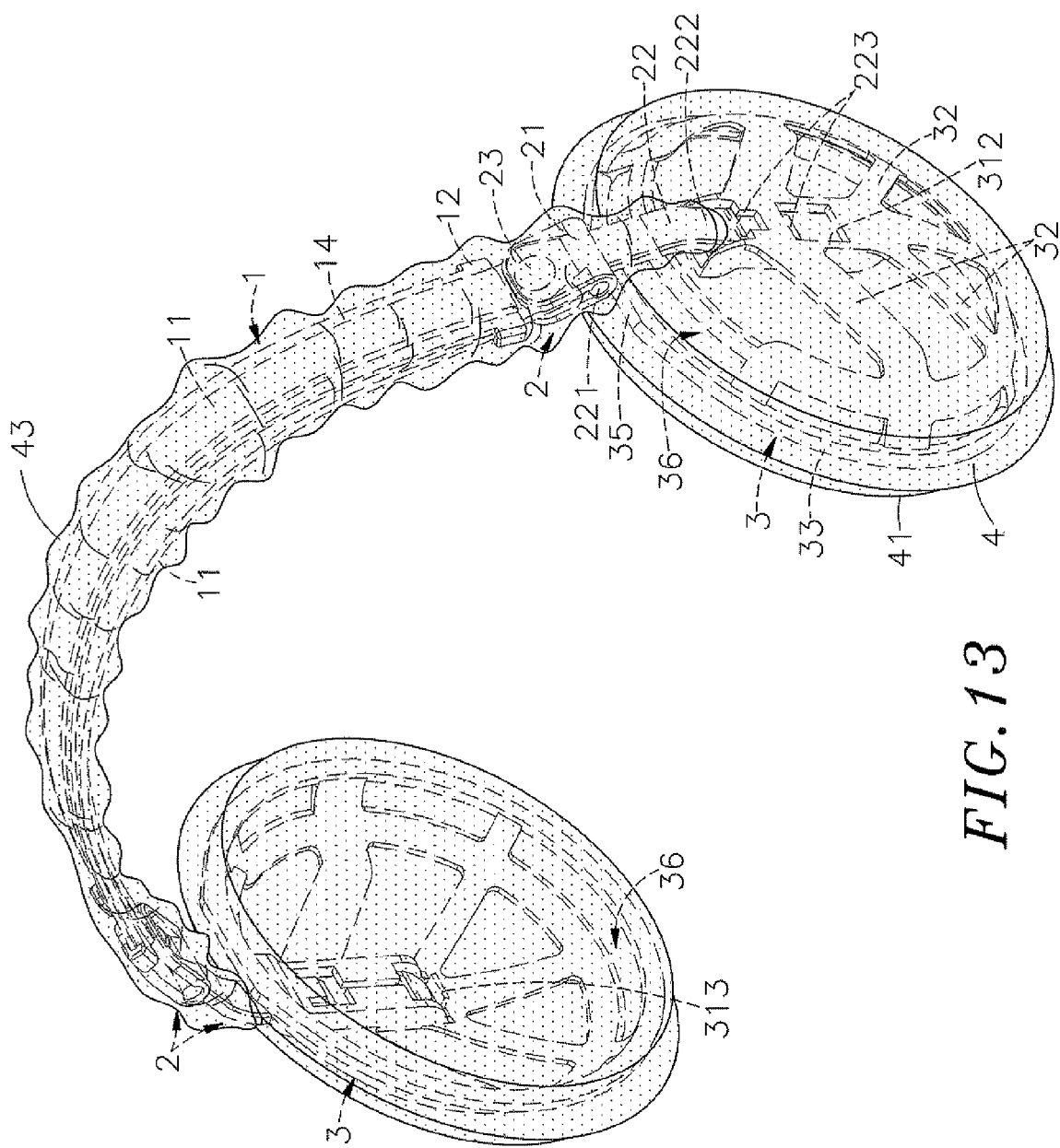
FIG. 13 is a schematic perspective view of the present invention, illustrating still another mounting arrangement of the soft fabric material.

Referring to FIG. 13, two narrow elongated pieces of the soft fabric material 4 can be stitched together to form a fabric tube 43 for surrounding the headband 1. The soft fabric material 4 can be spandex. Alternatively, the fabric tube 43 can be made in the form of an extendable bellows structure that fits length adjustment of the headband 1.

Figure 14:
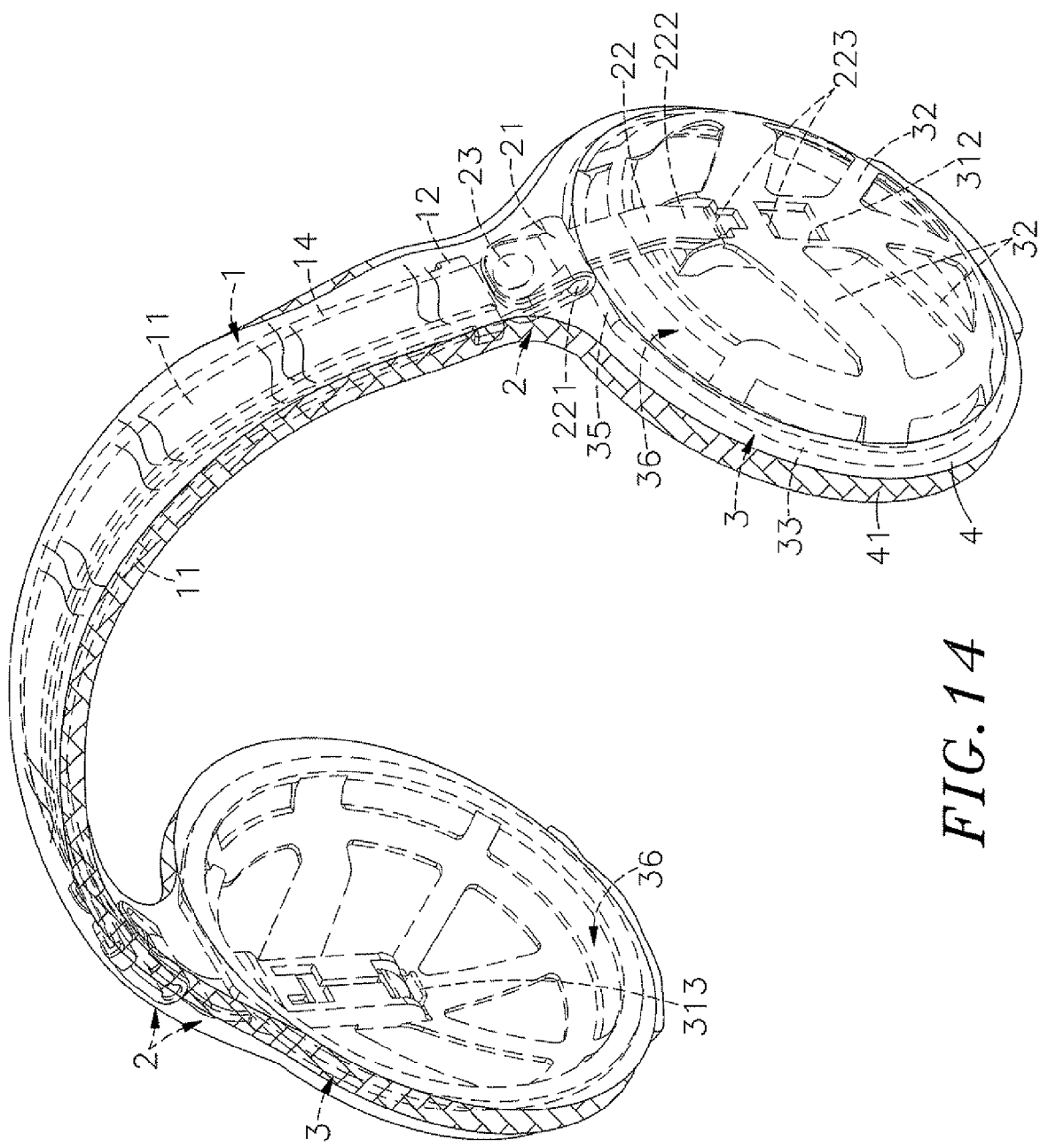
FIG. 14 is a schematic perspective view of the present invention, illustrating still another mounting arrangement of the soft fabric material.

Referring to FIG. 14, two pieces of the soft fabric material 4 can be attached to the top and bottom sides of the earmuff assembly and then peripherally stitched together to surround the headband 1, connection devices 2 and ear cups 3 of the earmuff assembly. Alternatively, two pieces of the soft fabric material 4 can be stitched together to form an earmuff covering with a small part of the peripheral edges of the pieces of the soft fabric material 4 left unstitched. The earmuff covering is turned inside out and then the earmuff is inserted into the earmuff covering. The unstitched peripheral edges around the opening at each of the two distal ends of the earmuff covering are respectively turned inwards and selectively inserted into the plug holes 36 of the ear cups 3.

Figure 15:
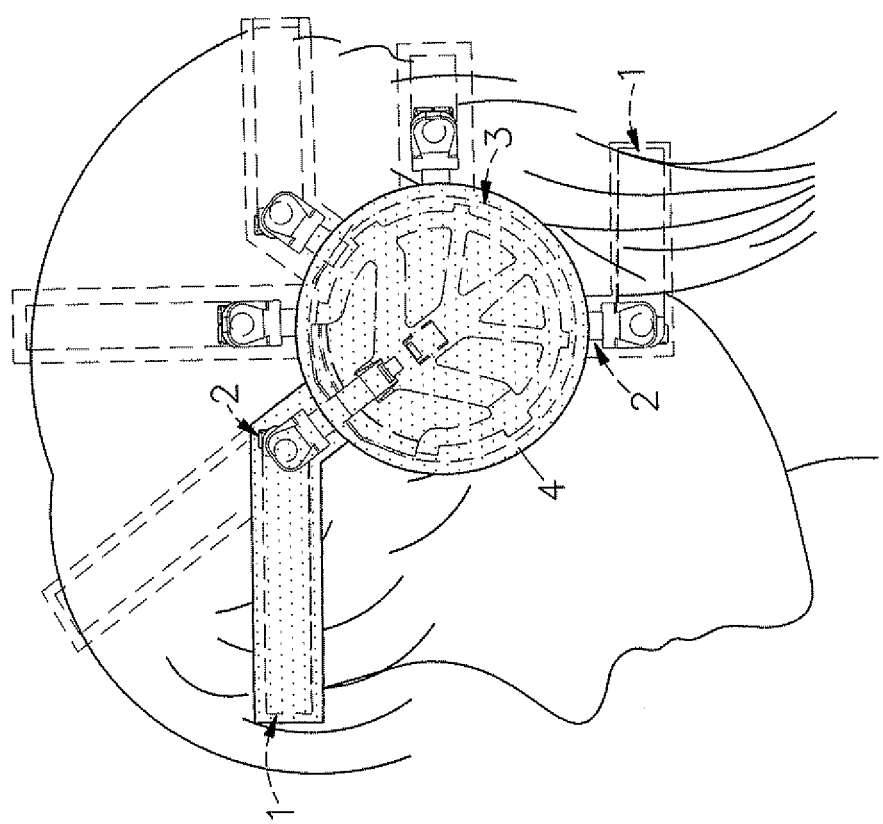
FIG. 15 is a schematic applied view of the earmuff assembly in accordance with the present invention.
Figure 16:
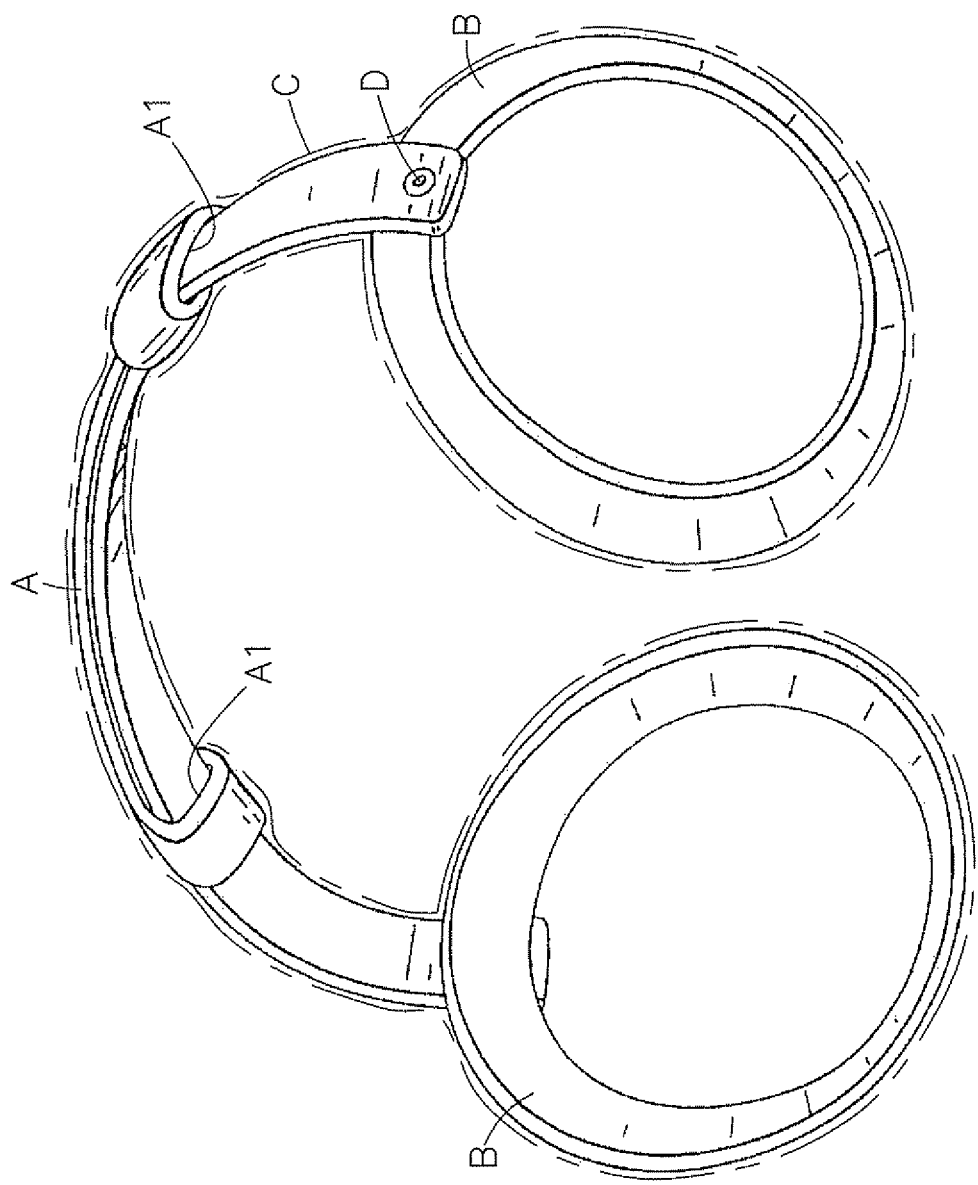
FIG. 16 illustrates the outer appearance of an earmuff assembly according to the prior art.

Referring to FIG. 15, subject to the connection arrangement of the connection devices 2 between the headband 1 and the ear cups 3, the user can conveniently adjust the angle of the ear cups 3 relative to the headband 1. For example, the user can attach the headband 1 to the forehead or the back or the top of the head, and then bias the ear cups 3 relative to the headband 1 to have the ear cups 3 be capped on the ears. By means of adjusting the combined length of the headband elements 11 of the headband 1 and the angles of the ear cups 3 relative to the headband 1, the earmuff assembly fits many hairstyles and satisfies many wearing requirements. When one is wearing a head covering, the earmuff assembly can be adjusted and worn over the head covering.

Although particular embodiments of the invention have been described in detail for purposes of illustration, various modifications and enhancements may be made without departing from the spirit and scope of the invention. Accordingly, the invention is not to be limited except as by the appended claims.

What the invention claimed is:

1. An earmuff assembly, comprising:
a headband consisting of two reversed headband elements, each said headband element comprising two constraint lugs bilaterally located on one end thereof, an insertion groove defined in each said constraint lug, a coupling portion located on an opposite end thereof, and two sliding grooves bilaterally extending along the length between the two opposite ends thereof, said coupling portion having two chamfered edges bilaterally located on a distal end thereof and a through hole spaced between said two chamfered edges, the coupling portion of one of said two headband elements being inserted through the insertion grooves of the constraint lugs of the other of said two headband elements to have the respective sliding grooves of one of said two headband elements be relatively slidably coupled to the respective insertion grooves of the other of said two headband elements, each said headband element having a thickness gradually increasing in direction from the constraint lugs toward the coupling portion;

two ear cups, each said ear cup comprising an elongated base frame, a rim, an insertion hole cut through two distal ends of said elongated base frame, a plurality of locating holes transversely formed in said elongated base frame across said insertion hole, a stop block located on one end of said insertion hole near the center of the respective ear cup, a plurality of ribs extending in transverse and radial directions and connected with one another between said base frame and said rim, a rounded accommodation space surrounded by said rim and said ribs, and a straight cutting edge located on the periphery of said rim adjacent to one end of said insertion hole and remote from said stop block;

two connection devices adapted for connecting said ear cups to said headband elements of said headband, each said connection device comprising a substantially U-shaped connection plate, an elongated connection strip and a pivot member, said U-shaped connection plate comprising a flat positioning space defined between two parallel ends thereof for receiving the coupling portion of one said headband element, a pivot hole cut through each of said two parallel ends across said flat positioning space, said pivot member pivotally connecting the pivot hole on each of the two parallel ends of said U-shaped connection plate to the through hole of the coupling portion of one said headband element, a round rod groove transversely located on a middle part of said U-shaped connection plate inside said positioning space, and an insertion slot cut through the middle part, said elongated connection strip comprising a strip body inserted through the insertion slot of said U-shaped connection plate, a round rod transversely located on and formed integral with one end of said strip body and pivotally positioned in the round rod groove of said U-shaped connection plate, and a plurality of locating teeth transversely located on and spaced along each of two opposite sides of said strip body remote from said round rod and selectively engaged with the locating holes of the elongated base frame of one said ear cup; and soft fabric cover means covering at least each of said two ear cups.

2. The earmuff assembly as claimed in claim 1, wherein the through hole of the coupling portion of each said headband element is pivotally connected to the pivot hole on each of the two parallel ends of the U-shaped connection plate of the respective connection device by the respective pivot member such that each said ear cup is biasable with the U-shaped connection plate of the respective connection device relative to said headband horizontally (in X-axis direction) to any one of 90°, 0° and 180° positions.

3. The earmuff assembly as claimed in claim 1, wherein said chamfered edges of said coupling portion of each said headband element are so made that each said ear cup is biasable with the U-shaped connection plate of the respective connection device relative to said headband horizontally (in X-axis direction) to any one of 90°, 0° and 180° positions.

4. The earmuff assembly as claimed in claim 1, wherein the connection arrangement between the round rod of each said connection device and the round rod groove of the associating U-shaped connection plate enables each said ear cup to be biased with the elongated connection strip of the respective connection device relative to said headband vertically (in Y-axis direction).

5. The earmuff assembly as claimed in claim 1, wherein each transversely extending locating tooth of the elongated connection strip of each said connection device comprises a beveled guide face located on a front side thereof and a vertical stop edge located on a rear side thereof.

6. The earmuff assembly as claimed in claim 1, wherein each said ear cup further comprises a plurality of plug holes defined in between said rim and said ribs and disposed adjacent to said straight cutting edge.

7. The earmuff assembly as claimed in claim 1, wherein each said ear cup further comprises a plurality of plug holes defined in between said rim and said ribs and disposed remote from said straight cutting edge.

8. The earmuff assembly as claimed in claim 1, wherein said soft fabric cover means comprises two soft fabric coverings, each said soft fabric covering comprising two pieces of soft fabric material respectively attached to one said ear cup and peripherally stitched together at the edges and a finding tape seamed to the stitched peripheral edges of said two pieces of soft fabric material.

9. The earmuff assembly as claimed in claim 1, wherein said soft fabric cover means comprises two soft fabric coverings, each said soft fabric covering comprising two pieces of soft fabric material peripherally stitched together to form a pocket having an opening for the insertion of one said ear cup.

10. The earmuff assembly as claimed in claim 1, wherein said soft fabric cover means is a single piece member covering said two ear cups, said headband and said two connection devices.

\* \* \* \* \*